United States Patent [19]

Kellett et al.

[11] 4,202,819
[45] May 13, 1980

[54] 2-(3-ALANYL)CLAVAM ANTIBIOTIC

[75] Inventors: Martha Kellett, Nutley; David Pruess; James P. Scannell, both of North Caldwell, all of N.J.

[73] Assignee: Hoffman-La Roche Inc., Nutley, N.J.

[21] Appl. No.: 35,884

[22] Filed: May 4, 1979

[51] Int. Cl.² .................... C07D 498/04; A61K 31/42
[52] U.S. Cl. ................................ 260/245.3; 424/272; 435/120; 435/886
[58] Field of Search ...................... 260/307 FA, 307 F

[56] References Cited

U.S. PATENT DOCUMENTS

| 4,048,186 | 9/1977 | Brown et al. | 260/307 FA |
| 4,093,626 | 6/1978 | Hunt | 260/307 FA |

*Primary Examiner*—Mark L. Berch

*Attorney, Agent, or Firm*—Jon S. Saxe; Bernard S. Leon; Frank P. Hoffman

[57] ABSTRACT

A novel bioactive substance of the formula

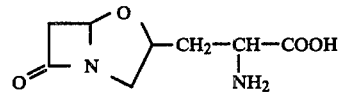

is produced in the fermentation of *Streptomyces clavuligerus*.

Also disclosed is a fermentation method of making the substance. The substance exhibits in vitro antimicrobial activity in defined minimal medium and antifungal activity in natural medium.

1 Claim, No Drawings

2-(3-ALANYL)CLAVAM ANTIBIOTIC

DESCRIPTION OF THE INVENTION

The present invention relates to an antibiotic substance of the formula

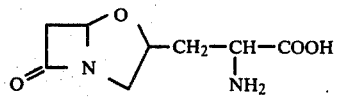

which is produced by the fermentation of *Streptomyces clavuligerus* (NRRL 3585 and ATCC 27064). The microorganism *Streptomyces clavuligerus* is a known microorganism having previously been utilized to produce the beta-lactamase inhibitors clavulanic acid (Belgian Pat. No. 827,926), beta-hydroxy-propionylclavulanic acid (German Pat. No. 2,708,047) and antifungal agents of the formula

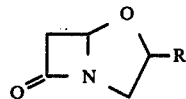

wherein R is $CH_2OH$,

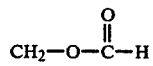

or COOH, (German Pat. No. 2,725,690 and South African Pat. No. 773,414).

The compound in its pure form exhibits in vitro antimicrobial activity against a variety of microorganisms and thus would be useful in wash solutions for sanitary purposes as in the washing of hands and the cleaning of equipment, floors and furnishings of contaminated rooms or laboratories. It is also useful for suppressing the growth of sensitive organisms in plate assays and other microbiological media.

The novel compound of the present invention has the chemical name 3-(7-oxo-4-oxa-1-azabicyclo[3.2.0]hept-3-yl)alanine or 2-(3-alanyl)clavam.

The compound is produced by the fermentation of a strain of *Streptomyces clavuligerus* (NRRL 3585 and ATCC 27064) and mutant strains derived therefrom. Morphological characteristics for this strain of *Streptomyces clavuligerus* are set forth in Belgian Pat. No. 827,926 which is incorporated herein by reference.

A fermentation broth containing *Streptomyces clavuligerus* is prepared by inoculating spores or mycelia of the clavulanic acid antibiotic producing organism into a suitable medium and then cultivating under aerobic conditions. For the production of the antibiotic, cultivation on a solid medium is possible but for production in large quantities cultivation in a liquid medium is preferable. The temperatue of the cultivation may be varied over a wide range, 20°–35° C., within which the organism may grow but a temperature of 26°–30° C. and a substantially neutral pH is preferred. In the submerged aerobic fermentation of the organism for the production of the antibiotic, the medium may contain as the source for carbon, a commercially available glyceride oil or a carbohydrate such as glycerol, maltose, lactose, dextrin, starch, etc. in pure or crude states and as the souce of nitrogen, an organic material such as soybean meal, distillers solubles, peanut meal, cotton seed meal, meat extract, peptone, fish meal, yeast extract, corn steep liquor, etc. and when desired inorganic sources of nitrogen such as nitrates and ammonium salts and mineral salts such as ammonium sulfate, magnesium sulfate and the like. It also may contain sodium chloride, potassium chloride, potassium phosphate and the like and buffering agents such as sodium citrate, calcium carbonate or phosphates and trace amounts of heavy metal salts. In aerated submerged culturing procedures, an anti-foam agent such as liquid paraffin, fatty oils or silicone compounds is used. More than one kind of carbon source, nitrogen source or anti-foam source may be used for production of the antibiotic. Generally the cultivation is continued until at least 40 mcg/ml of the antibiotic has accumulated in the medium.

The following Examples will serve to illustrate this invention without limiting it thereto.

EXAMPLE 1

*Streptomyces clavuligerus* NRRL-3585 was maintained on starch-casein agar slants. A portion of slant growth was used to inoculate 100 ml of TS+ broth in a 500 ml erlenmeyer flask. The flask was incubated at 28° C. on a rotary shaker for 2 days, at which time 20 ml of a sterile 50% glycerol was added and 4 to 6 ml of the resulting mixture were transferred to 10 ml screw capped test tubes. The tubes were immediately frozen in a dry ice bath and stored at −70° C. Inoculum was prepared by melting the frozen contents of the glass screw cap tube and transferring 10 ml of this growth into each of two six liter flasks.

The flasks each contained 2 liters of TS+ medium of the following composition:

| BBL Typticase Soy Broth dehydrated | 30 g |
|---|---|
| Glycerol | 10 g |
| Distilled water | 1 liter |
| No pH adjustment | |

The 6 liter flasks were incubated at 28° C. for 3 days on a rotary shaker. Good results were obtained with incubation times from one to four days. The 4 liters of growth were then used to inoculate 230 liters of a medium composed of:

| Glycerol | 20 g |
|---|---|
| Soyalose 105 (Central Soya) | 15 g |
| $K_2HPO_4$ | 1 g |
| $CoCl_2 6H_2O$ | 10 mg |
| SAG 4130 antifoam (Union Carbide) | 0.1 g |
| Tap water | 1 liter | pH 7.0 before sterilization, adjusted with 5 N $H_2SO_4$ in a 400 liter stainless steel fermentor.

EXAMPLE 2

Inoculum was prepared by placing 2 ml of the melted frozen growth utilized in Example 1 into 100 ml of TS+ medium in a 500 ml flask, shake for one day at 28° C., inoculate 6 liter flasks with 20 ml of this culture and then proceed as in Example 1.

EXAMPLE 3

The fermentation in a 400 liter fermentor was carried out at 28° C., with agitation at 150 RPM. The aeration rate was varied between 85 and 140 liters per minute in such a way that the dissolved oxygen level was maintained above 50% of saturation. The gauge pressure in the fermentor was 0.35 kg/cm$^2$ (5 psi). The pH was controlled between 6.5 and 7.5 by the addition of 5 N H$_2$SO$_4$ or 5 N NaOH solution as necessary.

The amount of antibiotic present in samples was determined by bioassay against Bacillus TA 1283B grown on the defined minimal medium of B. D. Davis and E. S. Mingioli (Mutants of *Escherichia coli* requiring methionine or vitamin B$_{12}$, J. Bact. 60, 17–28, 1950.

The fermentation was harvested after four days of incubation.

One hundred ninety liters of fermentation broth were harvested. Some 30–40 liters were taken as samples at intermediate points in the fermentation. The harvested broth (pH 7.2) was cooled to 20° C. and 1900 grams of Darco G-60 charcoal (ICI U.S. Wilmington, Del.) were added to it. The mixture was stirred gently for 15 minutes. The pH was adjusted to 6.5 with 100 ml of 5 N H$_2$SO$_4$, 6.8 kg of HyFlo Super Cel diatomaceous earth (Johns-Manville, Lompoc, Ca.) were added, and the mycelia were removed on a Bird rotary vacuum filter. The filter cake was washed with 22 liters of tap water.

The combined filtrate and water wash (210 liters, pH 7.7) were adjusted to pH 7.3 with 5 N H$_2$SO$_4$ and concentrated to a volume of 22 liters on a wiped film rotary vacuum evaporator (Model 08-032 TFP, Votator Div., Chemetron Corp., Louisville, Ky.).

The filtrate concentrate was loaded on a 30 cm diameter column containing 45 kg of Amberlite XAD-2 resin (Rohm and Haas, Philadelphia, Pa.) at a rate of 1.5 liters per minute. The concentrate was washed on carefully with deionized water.

The activity was eluted from the resin with 500 liters of deionized water. After salts appeared in the effluent, a series of twenty 20-liter cuts was taken. Based on assay data, cuts 2, 4, and 5 were concentrated on a flask evaporator to final volumes of 2.3, 2.2, and 2.7 liters respectively; cuts 6 and 7 were combined and concentrated to 2.3 liters; cut 3 was lyophilized in a freeze dryer (651 M Vac-Pac, Hull Corp., Hatboro, Pa.), yielding 175 grams of solids. Cut 3 contained most of the antibiotic, however the specific activities of cuts 4–7 were higher and the latter materials proved to be more suitable for further purification.

EXAMPLE 4

Ten grams from fraction 4 of the XAD-2 column was dissolved in about 30 ml of H$_2$O and filtered over a celite pad. The resulting clear amber solution (solids, 6.5 g in 38 ml final volume) was chromatographed on the Waters Prep LC $^{TM}$/System 500 using a 370 gram Prep PAK-500/C$_{18}$ column, with water elution. After the bed volume (400 ml), 100 ml fractions were collected and assayed biologically. The most active fractions obtained in the second bed volume were pooled and lyophilized to give 910 mg of solids.

A 900 mg portion of these solids was dissolved in water and rechromatographed on Bondapak $^{TM}$C$_{18}$/Porasil B (six 2 foot by ⅜ inch columns in series) with water elution. After the bed volume (approx. 90 ml), 5 ml fractions were collected. The peak bioactive fractions (#28 to 31) were pooled and lyophilized to give 105 mg of a slightly yellow solid. A 100 mg portion of these solids was dissolved in 1 ml H$_2$O, diluted with 1 ml methanol and applied to the top of a Sephadex LH-20 column (50 by 2.5 cm). The column was eluted with 4 bed volumes of methanol-water (1:1) and fifty 3 ml fractions were collected. The peak activity fractions (35–41) were pooled, concentrated to a small volume and ethanol was slowly added. The solution was chilled (approx. 4° C.) after which 17 mg of crystals were obtained. A second crop of 8 mg was recovered from the mother liquid.

EXAMPLE 5

A 10 g portion of lyophilized solids obtained from fractions 5–7 of the XAD-2 column previously described was slurried in 50 ml methanol-water (1—1) and filtered through a celite Hy-Flo filter pad. The combined filtrate and 50% CH$_3$OH—H$_2$O wash (75 ml final volume) was applied to the top of a column (50×15.5 cm i.d.) which contained 9 liters LH-20 gel in 50% methanol-water. The gel was eluted with the same solvent and the column was operated at 5° C. at a flow rate of 800 ml/hr. The peak active fraction was obtained at an elution volume 6.3–6.9 liters and was evaporated at reduced pressure with a water bath at 30° C. to a volume of 25 ml.

An 18 ml portion of this solution which contained 900 mg solids ws chromatographed with water on the Waters Prep LC $^{TM}$/System 500 using the Prep PAK-500/C$_{18}$ column. After the bed volume (400 ml) had been collected 20 fractions of 80 ml each were collected and bioassayed. The peak activity fractions (#6–9) were pooled and lyophilized to give 178 mg of a solid. The solid was dissolved in 1 ml of H$_2$O diluted with 1 ml methanol and applied to a 50 by 2.5 cm Sephadex LH-20 column which was eluted with four bed volumes of methanol-water (1:1). The peak bioactive fractions were pooled and concentrated in vacuo at 30° C., ethanol was added, the solution cooled to 4° C., and 20 mg of crystals recovered by filtration. Twenty mg of a second crop was recovered after standing at 4° C. overnight.

EXAMPLE 6

An aqueous solution (2 ml) of 760 mg crude antibiotic, obtained from the first LH-20 column as described in Example 5 was chromatographed on six, 2 foot by ⅜ inch Bondapak $^{TM}$D$_{18}$/Porasil B columns in series with water elution. After the bed volume (90 ml) fractions of 5 ml each were collected and bioassayed. The peak active fractions (#31–35) were pooled, concentrated in vacuo at 30° C. to approx. 1 ml of an aqueous solution. Addition of ethanol and chilling to 4° C. yielded 22 mg of crystalline antibiotic. $[\alpha]^{25} = -137.6(C=0.7, H_2O)$.

EXAMPLE 7

A 17 g portion of lyophilized solids from fraction 4 of the previously described XAD-2 column was slurried in 80 ml water at pH 6.6. Insoluble material, chiefly charcoal, was removed by filtration and the combined filtrate and water wash (final volume 100 ml) was applied to the top of a column (50×4.2 cm i.d.) containing 700 ml AG50W X-4, 100–200 mesh, resin in the Na$^+$ form. The resin was then washed and eluted with distilled water at 5° C. The peak activity was obtained at an elution volume of 400–500 ml after the appearance of unadsorbed substances in the effluent. The active fraction was concentrated to 2 ml from which crystals, 32 mg, were obtained from ½ (1 ml) of the solution after addition of 2 ml ethanol. The remaining 1 ml of solution was lyophilized to 48 mg residue from which additional crystalline material was subsequently obtained. m.p. 247–265 slow decomposition.

EXAMPLE 8

The in vitro antimicrobial activity of the antibiotic 5 (minimal inhibitory concentration) was determined by the agar diffusion well method. The results expressed in micrograms/ml were as follows:

What is claimed:
1. A substantially pure compound of the formula

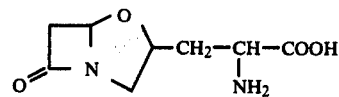

* * * * *

|  |  | Deposit No. | MIC (µg/ml) | |
|---|---|---|---|---|
|  |  |  | BBL Antibiotic Medium "A" Assay Agar | Davis Minimal Agar |
| G− rods | *Pseudomonas aeruginosa* 56 | ATCC 8709 | >1000 | >1000 |
|  | *Proteus vulgaris* 101N | ATCC 6380 | >1000 | * |
|  | *Escherichia coli* 94 | ATCC 27856 | >1000 | 1000 |
|  | *Klebsiella pneumoniae* 369 | ATCC 27858 | >1000 | 62.5 |
|  | *Serratia marcescens* SM | ATCC 27857 | >1000 | >500 |
|  | *Serratia sp.* 101 | ATCC 93 | >1000 | 500 |
|  | *Acinetobacter calcoaceticus* PCI-3 | ATCC 10153 | >1000 | >500 |
| G+ cocci | *Staphylococcus aureus* 82 | ATCC 6538 P | >1000 | * |
|  | *Sarcina lutea* PCI | ATCC 9341 | >1000 | >500 |
|  | *Streptococcus faecium* | ATCC 8043 | >1000 | * |
| G+ rods | *Bacillus megaterium* 164 | ATCC 8011 | >1000 | >500 |
|  | *Bacillus sp.* E | ATCC 27859 | >1000 | * |
|  | *Bacillus subtilis* 558 | NRRL 558 | >1000 | 0.25 |
|  | *Bacillus sp.* TA | ATCC 27860 | >1000 | 0.03 |
| G+ filaments | *Mycobacterium phlei* 78 | ATCC 355 | >1000 | >500 |
|  | *Streptomyces cellulosae* 097 | ATCC 3313 | >1000 | >500 |
| Molds | *Paecilomyces varioti* M16 | ATCC 26820 | 250 | 15.7 |
|  | *Penicillium digitatum* 0184 | ATCC 26821 | >1000 | * |
| Yeasts | *Candida albicans* 155 | NRRL 477 | >1000 | 500 |
|  | *Saccharomyces cerevisiae* 90 | ATCC 4226 | >1000 | 125 |

*Microorganism did not grow in minimal medium